United States Patent
Ozer et al.

(10) Patent No.: US 8,754,245 B2
(45) Date of Patent: *Jun. 17, 2014

(54) VAPOR-PHASE DECARBONYLATION PROCESS

(75) Inventors: Ronnie Ozer, Arden, DE (US); Ke Li, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 104 days.

This patent is subject to a terminal disclaimer.

(21) Appl. No.: 13/392,550

(22) PCT Filed: Aug. 31, 2010

(86) PCT No.: PCT/US2010/047208
§ 371 (c)(1),
(2), (4) Date: Feb. 27, 2012

(87) PCT Pub. No.: WO2011/026061
PCT Pub. Date: Mar. 3, 2011

(65) Prior Publication Data
US 2012/0165561 A1 Jun. 28, 2012

Related U.S. Application Data

(60) Provisional application No. 61/238,267, filed on Aug. 31, 2009.

(51) Int. Cl.
*C07D 307/36* (2006.01)
(52) U.S. Cl.
CPC .................................. *C07D 307/36* (2013.01)
USPC .......................................................... 549/506

(58) Field of Classification Search
CPC ...................................................... C07D 307/36
USPC ........................................................... 549/506
See application file for complete search history.

(56) References Cited

U.S. PATENT DOCUMENTS

| | | | |
|---|---|---|---|
| 2,634,276 A | 4/1953 | Carnahan |
| 3,007,941 A | 11/1961 | Copelin |
| 3,223,714 A | 12/1965 | Manly |
| 3,257,417 A | 6/1966 | Dunlop et al. |
| 3,663,295 A | 5/1972 | Baker |
| 4,774,221 A | 9/1988 | Medem |
| 4,780,552 A | 10/1988 | Wambach |

FOREIGN PATENT DOCUMENTS

| RU | 2027714 C1 | 1/1995 |
|---|---|---|
| SU | 1699601 A1 | 12/1991 |

OTHER PUBLICATIONS

U.S. Appl. No. 13/122,740, filed Apr. 6, 2011, Inventor Ronnie Ozer.
U.S. Appl. No. 13/392,541, filed Feb. 27, 2012, Inventor Ronnie Ozer.
U.S. Appl. No. 13/392,556, filed Feb. 27, 2012, Inventors Ronnie Ozer and Ke Li.
U.S. Appl. No. 13/124,574, filed, Apr. 15, 2011, Inventors Ronnie Ozer and Ke Li.

*Primary Examiner* — Taofiq A Solola

(57) ABSTRACT

A process is provided for the synthesis of furan and related compounds by vapor-phase decarbonylation of furfural and derivatives, using a palladium/metal aluminate catalyst that has been promoted with an alkali carbonate, such as cesium carbonate. The use of such catalysts, which are inherently less acidic than alumina, results in improved lifetime and high productivity.

13 Claims, No Drawings

VAPOR-PHASE DECARBONYLATION PROCESS

CROSS-REFERENCE TO RELATED APPLICATIONS

This application claims the benefit of U.S. Provisional Application No. 61/238,267, filed Aug. 31, 2009, which is incorporated in its entirety as a part hereof for all purposes.

FIELD OF DISCLOSURE

The disclosure relates to the manufacture of furan and related compounds, and to the industrial use thereof for the synthesis of other useful materials.

BACKGROUND

Furan and related compounds are useful starting materials for industrial chemicals for use as pharmaceuticals, herbicides, stabilizers, and polymers. For example, furan is used to make tetrahydrofuran, polytetramethylene glycol, polyether ester elastomers, and polyurethane elastomers.

Known transition metal catalyzed, vapor-phase processes to produce furan by decarbonylation of furfural are limited by either the selectivity or lifetime of the supported catalyst. The conversion of furfural to furan is complicated by the tendency to form polymeric or carbonizing byproducts which foul the catalyst surface and hinder the rate and lifetime of the catalyst. In the decarbonylation of furfural to furan, Pd has been shown to be an excellent catalyst for the reaction in both the liquid and vapor phases. The challenge of this chemistry has been deactivation of the catalyst from fouling reactions that are thought to proceed primarily through acid catalyzed oligomerization. Basic buffers have been added to the catalyst either as surface treatments (vapor phase) or as solid materials added to a liquid phase slurry reactor. Finding catalyst supports which enhance decarbonylation activity while minimizing deactivation reactions such as carbon fouling is important to the success of a Pd based process. Treating supports with basic buffers and base treatments has been shown to be effective in prior work, but a solid support that is active, stable and high temperature capable would have high value in this technology.

Supported palladium catalysts are known to catalyze furfural decarbonylation reaction with high selectivity but are limited by short lifetime. For example, U.S. Pat. No. 3,007,941 teaches a process for the production of furan from furfural comprising heating a liquid phase consisting essentially of furfural in the presence of palladium metal and a basic salt of an alkali metal; the basic salt is not part of the catalyst per se but is continuously added to the liquid phase during the reaction. Also, U.S. Pat. No. 3,257,417 a process for production of furan comprising contacting liquid furfural with a palladium catalyst in the presence of calcium acetate. Both these processes suffer from quick catalyst deactivation and difficult catalyst regeneration processes. U.S. Pat. No. 3,223,714 teaches a continuous low pressure vapor phase decarbonylation process for the production of furan comprising contacting furfural vapor with a supported palladium catalyst. A preferred catalyst has about 0.3 wt % Pd supported on alumina. The catalyst can be regenerated in situ but the lifetime of a running cycle for the catalyst is short and the production of furan per cycle is low. Catalysts which contain platinum and/or rhodium and to which cesium has been added are preferably used.

Co-pending U.S. Published Patent Application 2011/0196126 A1 hereby incorporated by reference in its entirety, provides a process for the vapor-phase decarbonylation of furfural to furan using heating a Pd/alumina catalyst that has been promoted with an alkali carbonate.

There remains a need for catalysts for the vapor phase and liquid phase decarbonylation of furfural to furan with improved lifetime and high productivity.

DESCRIPTION

The inventions disclosed herein include processes for the preparation of furan and related compounds and for the preparation of products into which those compounds can be converted.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

In one embodiment hereof, this invention provides a process for the synthesis of a compound as represented by the following structure of Formula (I)

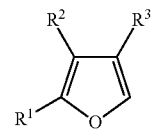

by providing a compound as represented by the following structure of Formula (II)

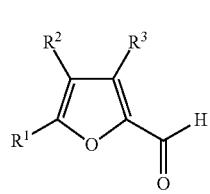

in the form of a gas, heating a Pd/metal aluminate catalyst, and contacting the Formula (II) compound and the catalyst to produce a Formula (I) product; wherein $R^1$, $R^2$, and $R^3$ are each independently selected from H and a $C_1$ to $C_4$ hydrocarbyl group.

In another embodiment hereof, a process is provided for preparing a Formula (I) product, as described above, that further includes promoting the Pd/metal aluminate catalyst with an alkali carbonate.

In another embodiment hereof, a process is provided for preparing a Formula (I) product comprising providing a compound as represented by Formula (II) in the form of a liquid, and heating the Formula (II) compound in a reactor in contact with a Pd/metal aluminate catalyst.

In another embodiment hereof, a process is provided for preparing a Formula (I) product, as in any of the processes described above, that further includes a step of subjecting the furan to a reaction (including a multi-step reaction) to prepare therefrom a compound (such as that useful as a monomer), oligomer or polymer.

An advantageous feature of the processes hereof is the increased lifetime and productivity of the Pd/metal aluminate catalyst and alkali carbonate-promoted Pd/metal aluminate catalyst versus other catalysts used previously.

In one embodiment of the processes described herein, $R^1$, $R^2$, and $R^3$ all equal H; thus, the Formula (I) product is furan and the Formula (II) compound is furfural. The decarbonylation of furfural to produce furan may then be represented by the following equation:

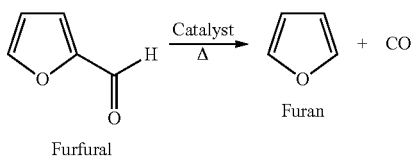

The Formula (II) compound used in the processes described herein is preferably obtained from a biological material which is a good source of hemicellulose. Examples include without limitation: straw, corn cobs, corn stalks (stover), sugar bagasse, hardwoods, cotton stalks, kenaf, oat hulls, and hemp. The Formula (II) compound, especially when it is furfural, should be freshly distilled before use, since it can oxidize and change color, producing undesirable high-boiling oxidation products.

In embodiments of the processes described herein, the decarbonylation reaction is catalyzed by a Pd/metal aluminate catalyst. As used herein, the term "metal aluminate" denotes a compound of alumina ($Al_2O_3$) with a metal oxide. Such a catalyst support is intrinsically less acidic than alumina. The use of such supports for the Pd which are intrinsically less acidic than $Al_2O_3$ results in less carbonization of the catalyst surface, reducing the rate of catalyst deactivation and thereby lengthening lifetime. Examples of suitable metal aluminates include without limitation aluminates of: alkali metals such as lithium, sodium, and potassium; alkaline earth metals such as calcium, barium, and strontium; lanthanum; gallium; and yttrium. An alkali metal aluminate may be prepared by reacting an alkali metal salt, such as an alkali metal carbonate, with a reactive transition alumina such as γ-alumina, at elevated temperatures, up to about 600° C.-700° C., for a period of up to 24 hours, as described in U.S. Pat. No. 3,663,295. Other metal aluminates may be prepared analogously. In one embodiment, the catalyst support is lithium aluminate, $LiAlO_2$ (CAS Registry No. 12003-67-7), which is available commercially (e.g., from Johnson Matthey, Royston Herts, England).

In another embodiment of the processes described herein, the decarbonylation reaction is catalyzed by a Pd/metal aluminate catalyst that has been promoted with an alkali carbonate, such as sodium carbonate ($Na_2CO_3$), potassium carbonate ($K_2CO_3$), or cesium carbonate ($Cs_2CO_3$). The alkali content of the catalyst is between about 1 and about 100 mg per g catalyst. In one embodiment, the alkali carbonate is cesium carbonate.

The catalyst is promoted by immersing a palladium/metal aluminate catalyst in the form of powder, pellets, rods, spheres or any extruded or pressed form in an aqueous solution of the alkali carbonate, with agitation. The concentration is the alkali carbonate solution not critical and is generally in the range of about 0.1 to about 20 wt %. Optimal immersion time will depend on the surface area of the palladium/metal aluminate catalyst, temperature, and alkali carbonate concentration and is readily determined by one of ordinary skill in the art. In one embodiment, the palladium/metal aluminate catalyst is immersed in a 5-10 wt % alkali carbonate solution at room temperature for about 4-6 hours. The wet catalyst is then removed from the solution and dried, for example, for about 2-3 hours in an air oven at about 110-130° C.; the catalyst may also be allowed to dry initially under ambient conditions, before oven drying. The dried catalyst is calcined at about 200 to 500° C. for about 2 to about 8 hours The decarbonylation reaction may be conducted as a vapor (gas) phase process or a liquid phase process. The terms "gas" and "vapor" are used herein interchangeably. In a vapor phase process, the reaction is conducted by injecting the Formula (II) compound in gaseous form into a reactor that is loaded with the desired catalyst. In one embodiment, the Formula (II) compound is provided in gaseous form by heating liquid Formula (II) compound to a temperature high enough to vaporize it; for furfural, this is about 180° C. A non-reactive internal standard (e.g., dodecane) may be present in the Formula (II) compound at about 0.5 wt % for analytical purposes, i.e., to confirm mass balance. Hydrogen may be co-fed to help volatilize the Formula (II) compound; hydrogen is also known to extend catalyst life. Typical hydrogen feed rates are from about 0.25 to about 5.0 moles hydrogen per mole furfural. Water may also be added to the Formula (II) compound, either in the liquid compound before it is volatilized or fed separately to either the liquid or gaseous Formula (II) compound, as described in co-pending U.S. Published Patent Application 2011/0196126 A1.

The reaction may occur in the gas phase at a temperature that may suitably be in the range of from about 200° C. to about 400° C., generally in the range of from about 270° C. to about 330° C. The reaction temperature referred to here is the temperature that has been provided for the catalyst in the catalyst zone of the reactor. A temperature in these ranges is provided by heating the various portions of the reactor from a source external thereto, in particular a heating element designed to surround and heat the catalyst zone of the reactor, and thus the catalyst itself. The selected temperature thus exists in the catalyst zone of the reactor upon the occasion when the furfural is contacted with the catalyst.

The vapor phase decarbonylation reaction is generally run at ambient pressure or slightly above. The pressure is not critical, as long as the Formula (I) and Formula (II) compounds remain in the gas phase in the reactor. The reaction residence time may be a minute or less, or about 5 to about 10 seconds, or about 1 to about 2 seconds, or less than one second. The reaction is run with continuously fed Formula (I) compound and, preferably, hydrogen for a length of time suitable to determine the lifetime of the catalyst. For example, a lifetime is calculated as the grams of furan produced per gram of Pd in the reactor. A lifetime of greater than 10,000 grams per gram Pd is desirable, greater than 100,000 grams per g Pd more so. In all cases, however, the reaction is carried out at a temperature and pressure and for a time that is sufficient to obtain gas-phase production of the Formula (I) compound. The amount of Pd is not critical; in one embodiment of the vapor phase process, it is present at 0.1 to 2.0 wt % (based on weight of total Pd+metal aluminate).

Supported Pd catalyst is known to degrade in activity over time through a number of mechanisms: 1) fouling, that is, the coating of the active sites with carbon ("carbonization"), 2) poisoning, that is, the disabling of active sites through reaction with process impurities, and 3) sintering, that is, the migration of Pd on the surface of the catalyst to produce a larger average Pd crystallite size and hence less available Pd surface for the reaction. The deactivation via pathway 1, carbonization, can be reversed through burning the carbon off the catalyst surface using an oxygen containing gas stream. However, Pd catalysts are known to be susceptible to deactivation via pathway 3, sintering, at temperatures normally associated with oxidative regeneration. The catalyst can instead be regenerated in a dilute oxygen stream with an excess of steam to draw the heat produced by the oxidative exotherm rapidly away from the catalyst surface. Dilution with nitrogen is also possible, though less preferable owing to its lack of heat capacity for cooling the catalyst bed. The regeneration may be done by feeding air and steam to the catalyst bed at a temperature range of between about 300° C. and about 500° C. with a composition of between about 2% and about 40% air for a time between about 10 seconds and about 100 hours.

In a liquid phase embodiment of the decarbonylation process, the reaction is conducted by injecting a Formula (II) compound in liquid form into a reactor that is loaded with the desired catalyst. The powder form of the Pd/metal aluminate catalyst can be used in liquid phase decarbonylation of Formula (II) compounds (e.g., furfural). In this case, the use of higher Pd loadings (about 1 to about 20% by weight; in one embodiment, about 2.5 to about 10% by weight) are used. Solids (catalyst) concentrations in the slurry reactor can be from 0.01 to 30 wt %; in one embodiment, the concentration is between 0.5 and 5 wt % catalyst. The Pd/metal aluminate catalyst powder can also be used with a basic buffer powder in suspension, such as sodium carbonate, potassium carbonate, or calcium acetate, as described in U.S. Pat. Nos. 3,007,941 and 3,257,417.

When the Formula (II) compound is furfural, the reaction may occur in the liquid phase at a temperature that may suitably be in the range of from about 162° C. to about 230° C., in the range of from about 190° C. to about 225° C., or in the range of from about 200° C. to about 220° C. The reaction temperature referred to here is the temperature that has been provided for the catalyst in the catalyst zone of the reactor. A temperature in these ranges is provided by heating the various portions of the reactor from a source external thereto, in particular a heating element designed to surround and heat the catalyst zone of the reactor, and thus the catalyst itself. The selected temperature thus exists in the catalyst zone of the reactor upon the occasion when the Formula (II) compound is contacted with the catalyst. When the atmospheric boiling point of the Formula (II) compound is lower than the reaction temperature, as is the case when the Formula (II) compound is furfural (boiling point about 162° C.), the reaction is run at greater than atmospheric pressure, for example, about 25 to 100 psi above atmospheric pressure. In addition to providing reflux temperatures in the desired range, such pressures facilitate the condensation and separation of the Formula (I) compound (e.g., furan) from the carbon monoxide gas stream produced as reaction proceeds.

Reactors suitable for use in the processes hereof include fixed-bed reactors, and pipe, tubular or other plug-flow reactors and the like in which the catalyst particles are held in place and do not move with respect to a fixed residence frame; or fluidized bed reactors. The Formula (II) compound may be flowed into and through reactors such as these on a continuous basis to give a corresponding continuous flow of product at the downstream end of the reactor. These and other suitable reactors are more particularly described, for example, in Fogler, *Elements of Chemical Reaction Engineering,* 2nd Edition, Prentice-Hall Inc. (1992). In one embodiment, in-flow lines are heat traced to keep the reactant at a suitable temperature, and the temperature of the catalyst zone is controlled by a separate heating element at that location. The Formula (I) product, as obtained from the reactor in the form of a gas, may be condensed by cooling to a liquid for ease of further handling. Alternatively, the process may further comprise purifying the Formula (I) product, such as by distillation. For example, the Formula (I) product may be fed directly into, e.g., a distillation column to remove unreacted Formula (II) compound and other impurities that may be present; the distilled product can then be isolated and recovered.

The distilled product may also, however, be subjected with or without recovery from the reaction mixture to further steps to convert it to another product such as another compound (such as a type useful, for example, as a monomer), or an oligomer or a polymer. Another embodiment of a process hereof thus provides a process for converting the Formula (I) product, through a reaction (including a multi-step reaction), into another compound, or into an oligomer or a polymer. For example, the Formula (I) product furan may be made from the Formula (II) compound furfural by a process such as described above, and then converted into tetrahydrofuran by dehydrogenation. The tetrahydrofuran can in turn be used for preparation of polytetramethylene ether glycol, which in turn can be reacted with 1,4-butanediol and terephthalic acid to produce polyetherester elastomers, or with diisocyanates to produce polyurethanes.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

The materials, methods, and examples herein are illustrative only and, except as specifically stated, are not intended to be limiting.

EXAMPLES

The advantageous attributes and effects of the processes hereof may be seen in a series of examples (Examples 1–3), as described below. The embodiments of these processes on which the examples are based are representative only, and the selection of those embodiments to illustrate the invention does not indicate that conditions, arrangements, approaches, regimes, steps, techniques, configurations, protocols or reactants not described in these examples are not suitable for practicing these processes, or that subject matter not described in these examples is excluded from the scope of the appended claims and equivalents thereof.

Materials.

The following materials were used in the examples.

Pd/alumina catalyst (0.5% Pd, gamma alumina support, 3 mm pellets) was obtained from the Engelhard Corporation, now BASF Catalysts LLC, a division of BASF—The Chemical Company, Ludwigshafen, Germany. Pd/lithium aluminate catalyst (0.5% Pd, lithium aluminate support, 3 mm pellets) was obtained from Johnson Matthey, Royston Herts, England.

Furfural was obtained from HHI, China, pre-distillation purity 98.5%. It was freshly distilled in a 20 plate 1 inch (2.54 cm) Oldershaw column batchwise prior to run with minimal air contact)

The meaning of abbreviations is as follows: "cm" means centimeter(s), "g" means gram(s), "GC" means gas chromatograph, "h" means hour(s), "kg" means kilogram(s), "mL" means milliliter(s), "min" means minutes, "mm" means millimeter(s), "psig" means pounds per square inch gauge, "THF" means tetrahydrofuran, and "vol" means volume.

Comparative Example A

This comparative example demonstrates the vapor-phase decarbonylation of furfural in the presence of an unpromoted Pd/alumina catalyst.

Approximately 2 grams of Pd/alumina catalyst (0.5% Pd on gamma alumina support, 3 mm pellets) was loaded onto a stainless steel mesh support within a 18"×½" (45.7 cm×1.3 cm) outside diameter (o.d.) type 316 stainless steel tube reactor with inlets for gas and liquid feeds and an internal thermocouple operating at atmospheric pressure. The catalyst was then pre-conditioned in situ in the reactor by flowing nitrogen gas, initially at room temperature, then raising the temperature to 270° C. over a period of 2 hours, while flowing hydrogen gas at 15 cm³/min, and introducing the furfural feed (which included 0.5 wt % dodecane as an internal standard) concurrently to generate reaction data. At reaction temperature (270° C.), hydrogen flow was set at 17 mL/min and furfural flow at 2.0 mL/h. The molar ratio of hydrogen to furfural was 2.0. The gaseous product stream was kept at 180° C. and fed directly to an Agilent™ 6890 GC equipped with flame ionization and mass selective detectors. Furfural conversion (%) was calculated as follows: [(1−(area % furfural in product/area % dodecane in the product)/(area % furfural in feed liquid/area % dodecane in feed liquid)] times 100. Furan selectivity (%) was calculated as follows: (moles of furan/ moles of furfural reacted) times 100. THF, furfural alcohol and methyl-furan selectivity (%) were calculated analogously. Kilograms of furan produced per gram of Pd was calculated using the conversion, the furan selectivity and the amount of Pd in the reactor during the lifetime study. Initial furfural conversion was 99%, but it steadily dropped during the run to 93% at 23 hours (3.06 kg furan per g Pd), and to 32% at 126 hours (7.87 kg furan per g Pd). Furan selectivity was 83% initially, with 12% selectivity to tetrahydrofuran (THF). At 23 hours Furan selectivity was 92% with 3% selectivity to THF. At 126 hours, the furan selectivity had dropped to 89% with 0.3% THF. Byproducts were primarily 2-methylfuran and furanmethanol, both from hydrogenation of furfural.

TABLE 1

| Hours | Kg Furan per g Pd | Furfural Conversion % | THF Selectivity % | Furan Selectivity % |
|---|---|---|---|---|
| 1 | 0.1 | 99 | 12 | 83 |
| 23 | 3.06 | 93 | 3 | 92 |
| 126 | 7.87 | 83 | 0.3 | 89 |

Comparative Example B

This example demonstrates preparation of a $Cs_2CO_3$-promoted Pd/alumina catalyst.

The Pd/alumina catalyst described in Comparative Example A (0.5% Pd, 20.3125 g) was immersed in 20 mL of a 7.5% aqueous solution of $Cs_2CO_3$ (1.50 g $Cs_2CO_3$ in 20 mL deionized water) and gently agitated on an orbital shaker for 5 hours at room temperature. The mixture was filtered and the rods rinsed with deionized water (3×20 mL). The rods were allowed to air dry. The catalyst was further dried in an oven at 120° C. in ambient air for 2 hours and cooled to room temperature for 1 hour and weighed. The rods were calcined at 300° C. for 4 hours and cooled overnight.

Comparative Example C

This example demonstrates the vapor-phase decarbonylation of furfural in the presence of a Pd/alumina catalyst that was promoted with cesium carbonate.

The procedure similar to that described in Comparative Example A was carried out using Pd/alumina catalyst that was treated with cesium carbonate using the procedure of Comparative Example B. Approximately 2 grams of Pd/alumina catalyst (0.5% Pd on gamma alumina support, 3 mm pellets) was loaded onto a stainless steel mesh support within a 18"× ½" (45.7 cm×1.3 cm) outside diameter (o.d.) type 316 stainless steel tube reactor with inlets for gas and liquid feeds and an internal thermocouple operating at atmospheric pressure. The catalyst was then pre-conditioned in situ in the reactor by flowing nitrogen gas, initially at room temperature, then raising the temperature to 290° C. over a period of 2 hours, while flowing hydrogen gas at 15 cm³/min, and introducing the furfural feed (which included 0.5 wt % dodecane as an internal standard and 3% water by weight) concurrently to generate reaction data. At reaction temperature (290° C.), hydrogen flow was set at 17 mL/min and furfural flow at 2.0 mL/h. The molar ratio of hydrogen to furfural was 2.0. The gaseous product stream was sampled by condensing a 15 minute flow time in a chilled (−10 C) glass product bottle which contained 0.5 ml n-methylpyrrolidone (NMP) for sample dilution. The sample was injected into an Agilent™ 6890 GC equipped with flame ionization and mass selective detectors. Furfural conversion (%) and product selectivity (%) were determined by GC analysis as described in Comparative Example A. The initial furfural conversion was 99.2%. The furfural conversion was steady until approximately 139 hours (21.2 kg furan per g Pd) when unconverted furfural began growing in the GC analysis showing 87.1% conversion. The reactor temperature was then raised to 310° C. to increase the furfural conversion. At 144.5 hours the furfural conversion was up to 94.6%. At 163.8 hours the conversion was at 90.4% and the temperature was raised to 330 C for one more day of operation (25.8 kg furan per g Pd). The furfural feed was stopped at 171 hours. Furan selectivity was 94.1% initially, with 4.8% selectivity to tetrahydrofuran (THF). At 139 hours, furan selectivity was 97.8% with 0.3% selectivity to THF. At 171 hours, the furan selectivity was 98.6% with minimal THF production. Less than 1% byproduct methylfuran and furanmethanol was seen throughout the run.

TABLE 2

| Temperature, °C. | Hours | Kg Furan per g Pd | Furfural Conversion % | THF Selectivity % | Furan Selectivity % |
|---|---|---|---|---|---|
| 290 | 1 | 0.1 | 99.2 | 4.8 | 94.1 |
| 290 | 139.2 | 21.2 | 87.1 | 0.3 | 97.8 |
| 310 | 144.5 | 21.9 | 94.6 | 0.2 | 98.3 |
| 310 | 163.8 | 25.2 | 90.4 | 0.2 | 98.3 |
| 330 | 171 | 26.3 | 95.4 | 0.1 | 98.6 |

Example 1

This example demonstrates the vapor-phase decarbonylation of furfural in the presence of unpromoted Pd/lithium aluminate catalyst.

The procedure described in Comparative Example C was carried out using Pd/lithium aluminate catalyst that was not pre-treated in any way. Furfural conversion and product selectivity (%) were determined by GC analysis as described in Comparative Example A. The initial furfural conversion was 100%. The furfural conversion was slowly decreasing until approximately 116 hours (17.5 kg furan per g Pd) when the conversion was at 98.8% but selectivity to furfuryl alcohol (furanmethanol) had climbed to 2.5%. The reactor temperature was then raised to 310° C. to improve furfural conversion and selectivity to furan. At 120 hours the furfural conversion was up to 99.4% and furfuryl alcohol was down to 0.5%. At 169 hours the conversion was at 88.5% and the temperature was raised to 330° C. for one more day of operation (27.1 kg furan per g Pd was reached). The furfural feed was stopped at 191 hours as conversion continued to drop. Furan selectivity was 70.4% initially, with 26% selectivity to tetrahydrofuran (THF). At 120 hours, furan selectivity was 95.2% with 2.5% selectivity to THF. At 169 hours, the furan selectivity was 93% with 1.3% THF production. Byproduct 2-methylfuran was initially at 1.7%, but dropped below 0.5% after only 2 hours of operation and remained low throughout the run.

TABLE 3

| Temperature, °C. | Hours | Kg Furan per g Pd | Furfural Conversion % | THF Selectivity % | Methyl Furan Selectivity % | Furfuryl Alcohol Selectivity % | Furan Selectivity % |
|---|---|---|---|---|---|---|---|
| 290 | 1 | 0.1 | 100 | 26 | 1.7 | 0.0 | 70.4 |
| 290 | 116 | 17.5 | 98.8 | 4.4 | 0.7 | 2.5 | 90.9 |
| 310 | 120 | 18.0 | 99.6 | 2.2 | 0.5 | 0.9 | 95.1 |
| 310 | 169 | 24.9 | 88.5 | 1.3 | 0.5 | 3.5 | 93.0 |
| 330 | 191 | 27.1 | 67.5 | 0.6 | 0.4 | 2.3 | 95.6 |

Example 2

This example demonstrates the vapor-phase decarbonylation of furfural in the presence of a Pd/Li-alumina catalyst that was promoted with cesium carbonate.

The procedure, similar to that described in Comparative Example A, was carried out using Pd/Li-alumina catalyst that had been treated with cesium carbonate using the procedure of Comparative Example B. Approximately 2 grams of Pd/lithium aluminate catalyst (0.5% Pd on lithium aluminate support, 3 mm pellets) was loaded onto a stainless steel mesh support within a 18"×½" (45.7 cm×1.3 cm) outside diameter (o.d.) type 316 stainless steel tube reactor with inlets for gas and liquid feeds and an internal thermocouple operating at atmospheric pressure. The catalyst was then pre-conditioned in situ in the reactor by flowing nitrogen gas, initially at room temperature, then raising the temperature to 290° C. over a period of 2 hours while flowing hydrogen gas at 15 cm$^3$/min, and introducing the furfural feed (which included 0.5 wt % dodecane as an internal standard and 3% water by weight) concurrently to generate reaction data. At reaction temperature (290° C.), hydrogen flow was set at 17 mL/min and furfural flow at 2.0 mL/h. The molar ratio of hydrogen to furfural was 2.0. The gaseous product stream was sampled by condensing a 15 minute flow time in a chilled (−10° C.) glass product bottle which contained 0.5 mL n-methylpyrrolidone (NMP) for sample dilution. Furfural conversion and product selectivity (%) were determined by GC analysis as described in Comparative Example A. The results, shown in Table 4, demonstrate a longer lifetime with alkali-promoted Pd on lithium aluminate than seen on alkali-promoted alumina as well as non promoted Li-aluminate. The alkali carbonate treatment significantly reduced hydrogenation activity in the decarbonylation process.

TABLE 4

| Temp °C. | Hours | Kg Furan per g Pd | Furfural Conversion % | THF Selectivity % | Furfuryl Alcohol Selectivity % | Furan Selectivity % |
|---|---|---|---|---|---|---|
| 290 | 1 | 0.16 | 100 | 1.0 | 0.0 | 97.6 |
| 290 | 120 | 18.3 | 95.0 | 0.1 | 4.2 | 95.0 |
| 310 | 149 | 22.4 | 95.0 | 0.0 | 2.6 | 96.3 |
| 310 | 196.8 | 29.5 | 95.6 | 0.1 | 3.4 | 95.5 |
| 310 | 287 | 42.7 | 92.0 | 0.1 | 2.8 | 96.1 |

Example 3

This example demonstrates the liquid-phase decarbonylation of furfural to furan using a Pd/metal aluminate catalyst.

Dry furfural (60.07 g) and catalyst (0.3 g, 5% Pd on alumina/lithium aluminate) were charged to a 100-mL stainless steel Parr reactor equipped with a mechanical agitator, furfural feed line and vertical stainless steel condenser, contained by a pressure-regulated vent valve. The vertical condenser was maintained at a temperature to return unreacted furfural to the reactor while allowing furan and carbon monoxide vapor to pass through the pressure-regulated vent valve, after which the furan product was condensed, and the carbon monoxide production rate was measured using a mass flow meter.

The reaction charge was heated, and the temperature was automatically controlled at about 190° C. The pressure-regulated vent valve was adjusted to maintain about 21 psig pressure on the reactor contents. The reaction was run substantially according to the procedure described in Example 1 of U.S. Pat. No. 3,257,417, except that the temperature was about 190° C. instead of about 215° C. and the pressure was about 21 psig instead of about 67 psig. Furfural was initially fed to the reactor at a rate of about 7.5 mL/h. The measured carbon monoxide production rate with time showed about a 75% decrease in catalyst activity over about 20 h of reaction time. The initial rate of 231 g furan per g Pd per hour dropped to about 49 after 20 h.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

What is claimed is:

1. A process for the synthesis of a compound as represented by the following structure of Formula (I)

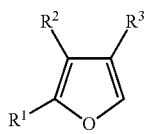

I by providing a compound as represented by the following structure of Formula (II)

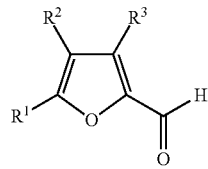

II in the form of a gas, heating a Pd/metal aluminate catalyst that has been promoted with an alkali carbonate, and contacting the Formula (II) compound and the catalyst to produce a Formula (I) product;

wherein $R^1$, $R^2$, and $R^3$ are each independently selected from H and a $C_1$ to $C_4$ hydrocarbyl group.

2. The process according to claim 1 wherein $R^1$, $R^2$, and $R^3$ are each H.

3. The process according to claim 1 wherein the metal aluminate is an alkali metal aluminate, an alkaline earth metal aluminate, gallium aluminate, lanthanum aluminate, or yttrium aluminate.

4. The process according to claim 3 wherein the alkali metal aluminate is $LiAlO_2$.

5. The process according to claim 1 wherein the alkali carbonate is cesium carbonate.

6. The process according to claim 1 where the alkali content of the promoted catalyst is between 1 and 100 mg per g catalyst.

7. The process according to claim 1 wherein hydrogen is co-fed with the Formula (II) compound.

8. The process according to claim 1 wherein water is added to the Formula (II) compound.

9. The process according to claim 1 wherein contacting the Formula (II) compound and the catalyst to produce a Formula (I) product occurs in the gas phase at a temperature that is in the range of from about 200° C. to about 400° C.

10. The process according to claim 9 wherein the temperature is in the range of from about 270° C. to about 330° C.

11. The process according to claim 1, further comprising purifying the Formula (I) product.

12. The process according to claim 11, wherein the Formula (I) product is purified by distillation.

13. The process according to claim 1 further comprising a step of subjecting the Formula (I) compound to a reaction to prepare therefrom a compound, oligomer or polymer.

* * * * *